(12) United States Patent
Voegeli et al.

(10) Patent No.: US 8,445,030 B2
(45) Date of Patent: May 21, 2013

(54) PERSISTENT AND FAST ACTING ANTISEPTICS AND DISINFECTANTS BASED ON CALCIUM FLUORIDE

(76) Inventors: Fridolin Voegeli, Thalwil (CH); Frank Flechsig, Wohlen (CH); Thomas Flechsig, Hermetschwil (CH)

( * ) Notice: Subject to any disclaimer, the term of this patent is extended or adjusted under 35 U.S.C. 154(b) by 233 days.

(21) Appl. No.: 12/882,296

(22) Filed: Sep. 15, 2010

(65) Prior Publication Data

US 2011/0064829 A1   Mar. 17, 2011

Related U.S. Application Data

(60) Provisional application No. 61/242,417, filed on Sep. 15, 2009, provisional application No. 61/247,675, filed on Oct. 1, 2009, provisional application No. 61/351,392, filed on Jun. 4, 2010.

(51) Int. Cl.
| | | |
|---|---|---|
| *A01N 25/00* | (2006.01) | |
| *A01N 25/02* | (2006.01) | |
| *A01N 25/24* | (2006.01) | |
| *A61K 31/19* | (2006.01) | |
| *A61K 31/191* | (2006.01) | |
| *A61K 31/192* | (2006.01) | |
| *A61K 31/194* | (2006.01) | |
| *A61K 31/216* | (2006.01) | |
| *A61K 33/16* | (2006.01) | |
| *A61K 33/20* | (2006.01) | |

(52) U.S. Cl.
USPC ........... 424/675; 424/405; 424/407; 424/601; 424/661; 424/673; 514/553; 514/557; 514/568; 514/572; 514/574

(58) Field of Classification Search
USPC .. 424/405, 407, 601, 661, 673, 675; 514/553, 514/557, 568, 572, 574
See application file for complete search history.

(56) References Cited

U.S. PATENT DOCUMENTS

| | | | |
|---|---|---|---|
| 1,702,103 A | | 2/1929 | Blumenberg |
| 3,377,279 A | * | 4/1968 | Sibert ........................... 508/129 |
| 5,145,668 A | | 9/1992 | Chow et al. |
| 5,476,647 A | | 12/1995 | Chow et al. |
| 5,718,908 A | * | 2/1998 | Fanelli ......................... 424/401 |
| 6,110,908 A | | 8/2000 | Guthery |
| 6,939,859 B1 | * | 9/2005 | Murase et al. ................. 514/27 |

FOREIGN PATENT DOCUMENTS

WO    WO-8605359    9/1986

OTHER PUBLICATIONS 2007-2008 Aldrich Catalog, pp. 593-594 (calcium fluoride entry) and pp. 2863 (particle size conversion table).*
"Pharmaceutical Dosage Forms, vol. 2", Herbert A. Lieberman and Leon Lachman, eds., Marcel Dekker, Inc.: New York, 1981, pp. 77-85.*

\* cited by examiner

*Primary Examiner* — James H. Alstrum-Acevedo
(74) *Attorney, Agent, or Firm* — Gifford, Krass, Sprinkle, Anderson & Citkowski, P.C.

(57) ABSTRACT

Antiseptic compounds that act as persistent and fast acting antiseptics and disinfectants. The base of these antiseptic actions is $CaF_2$ as the persistent part, preventing the colonization of tissue and nonliving surfaces with microorganisms through the targeted on-demand release of fluorine ions. For fighting heavy contamination and invasion of transient microbes through new application of the solution, fast acting alcohols and toxic solutions have been added in small percentage. They act fast and evaporate fast, leaving the natural protection of skin undamaged and coated with a persistent antiseptic.

9 Claims, No Drawings

PERSISTENT AND FAST ACTING ANTISEPTICS AND DISINFECTANTS BASED ON CALCIUM FLUORIDE

CROSS-REFERENCE TO RELATED APPLICATIONS

This application claims priority of U.S. Provisional Patent Application Ser. No. 61/242,417 filed Sep. 15, 2009; Ser. No. 61/247,675 filed Oct. 1, 2009; and Ser. No. 61/351,392 filed Jun. 4, 2010, which are incorporated herein by reference.

FIELD OF THE INVENTION

The present invention relates to antiseptic solution compositions useful in medical clinical and in public environments for topical and systemic disinfection.

BACKGROUND OF THE INVENTION

Antiseptics are antimicrobial chemical substances that are applied to living tissue/skin to reduce the possibility of infection, sepsis or putrefaction caused by microorganisms, and disinfectants destroy microorganisms found on nonliving objects.

In the second half of the nineteenth century, inspired by Louis Pasteur's germ theory of disease, the doctors Lister, Semmelweis, Tichenor and others introduced antiseptic treatment and surgical methods into their daily work and initiated a completely new quality of medicine: open wounds, surgery, and infectious diseases no longer led to painful death but were cured through topical antiseptics, and later by internal antibiotics.

Many powerful and fast acting antiseptics have been developed by chemists and applied by doctors and households; some have been abandoned because they produced side effects, others because they were just too inexpensive and not sufficiently profitable to the medical industry; a handful, mainly alcohol based antiseptics, became standards.

From the beginning Pasteur and his followers stipulated that disinfection and antiseptic methods are not 100% effective procedures and have to be verified and classified using the "killing rate" on the specific microorganisms reached and attacked by the disinfecting agent. Today we apply "fast acting" and "persistent" topical antiseptics that all should be "broad spectrum", i.e. effective against a variety of microorganisms. Fast acting antiseptics are measured by significant reduction in strength determined by cultures obtained a few moments (less than minutes) following application of the antiseptic.

The quality of "persistence" refers to the ability of the antiseptic to continue to kill once it is applied and is due to the retention or binding of the chemical in the stratum corneum of the skin after partial evaporation and after rinsing. It is measured by the time for the micro-flora to be restored to the baseline which existed before the application.

Currently there are several fast acting antiseptics, effective within 20 seconds against transient microorganisms which could cause infections. Most of these antiseptics are based on alcohols, iodine solutions, or chlorides. However all these fast acting antiseptics cannot prevent fast repopulation of the depleted (mainly evaporated) "killing ground" where also all the natural body protection (fatty acids, different salts, regulated pH 5.4-5.5) against invasions has been destroyed.

Persistence, as applied in food industry or exhibited in ancient embalming practices, has remained an elusive goal of medical antiseptic technology. Regulating bodies like the FDA have required persistence since the 1970s for any new antiseptic to be approved, with very little response, actually enhancing the utilization of outdated, nonpersistent, alcohol based disinfectants. Additional regulations for new antiseptics to be tested and evaluated as "medications", in lengthy and costly clinical trials, led to an end to all small enterprise chemical development and production of innovative disinfectants.

Nature has produced the bill: The surviving microorganisms evolved to develop resistance to short acting threats that allow them to immediately recolonize the tissue cleansed by the short persistence antimicrobials with the next transient flora from the next patient or from the next hand grip.

Best practice now requires doctors and care personnel to wash their hands with antiseptics before and after each patient, X times a day! The campaign "Clean Hands" in German hospitals mounted dispenser bottles for disinfectants on each patient's bed, because the walk to the room's door and back would add up to miles and hours every day. But the doctors and caregivers just cannot do it X times a day without heavy damage to their skin and their health. Compliance therefore remains low and the microorganisms are "taking over": In Germany every year some 800,000 patients (1 out of 20!) fall seriously ill by in-hospital infections; the number of fatal casualties are kept secret by the hospital companies.

SUMMARY OF THE INVENTION

The present invention is therefore directed to novel antiseptics and disinfectants which have been designed "bottom up" based on minerals that act as persistent "aseptics" and prevent microorganism from colonizing nonliving surfaces and skin tissue, while maintaining and eventually enforcing the skin's natural protection flora and mechanisms.

In addition to this persistent preventive action, when heavy contamination and invasion of transient microbes requires a new application of the solution, fast acting alcohols and toxic solutions have been added in small percentage. They act fast on the new microorganisms and then evaporate fast, without damaging the natural protection of skin and persistent antiseptic.

The compounds of the present invention include:
1) As a base, a natural fine mineral, preferably calcium fluoride ($CaF_2$), which exhibits a high killing rate on most microorganisms. This mineral is extremely persistent, sticking to the skin or to surface paints for long periods and releasing its killing fluorine ions only "on demand" when there is moisture and warmth. The mineral is extremely stable, releasing into aqueous solution only 16 mg/l water (=16 ppm) and rebinding immediately when the surface becomes dry again. ($CaF_2$ is mined underground in Germany; in some of these mines underground ponds with water thousands of years old are used as miraculous "fountains of youth" and health baths by the local population.) The $CaF_2$ is used in a fine milled form with particles in the range of 0.25-5.0 microns and preferably 0.5-2.5 microns.
2) When in solution $CaF_2$ also releases calcium ions, basic building blocks for skin, bones, teeth, and other body tissues, enforcing them against any damage and supporting the healing and recovery of cuts, abrasion, and general wounds. This free calcium captures other fluorine ions that could be harmful in too high doses.
3) $CaF_2$ has the same pH 5.4 as normal skin (pH 5.4-5.5). It does not degrade the self-defense mechanisms of the skin, as do soaps.
4) Highly toxic and therefore highly efficient antiseptics are added in very low percentage, initiating and amplifying fast antiseptic action on microorganisms when newly applied as a wash to the tissue: e.g. 0.2-2.0% Eau de Javel (KClO) or 10% ethanol work well. In medical hand wash they act fast, then evaporate and release the skin surface with no damage, with the persistent $CaF_2$ still in place.

5) Well known and accepted drugs are added in low percentage, to stabilize and prevent growth of multi-cellular microorganisms like fungi and mildew that are not attacked by the basic $CaF_2$ ions, thus making the compound really "broad spectrum": e.g. 0.6% esters of salicylic acids work well as fungicide in this compound.

After medical investigation, treatment, or transport, the caregivers can wash their hands X times a day with a new hand wash of these compounds: new transient microbes are killed fast, recolonization is still prevented by the updated $CaF_2+$ layer.

The following tables show some formulations of the present invention with different grade of skin/tissue protection and cure.

EXAMPLE 1

Formulation for $CaF_2$-Based Antiseptic Spray

| Active Agent | Mass % | mg/l | Solubility |
|---|---|---|---|
| $H_2O$ (water) | 98 | 980000 | |
| $CaF_2$ (calcium fluoride) | 0.005 | 50 | 16 ppm |
| Cinnamic acid | 0.05 | 500 | high |
| Aspirin ester | 0.25 | 2500 | high |
| Quinic acid | 0.1 | 1000 | very high |
| NaOCl (Javel water 2.5%) | 0.075 | 750 | as ester |
| $H_2O_2$ (hydrogen peroxide 27%) | 1.2 | 12000 | very high |
| Citric acid | 0.42 | 4200 | very high |

Antimicrobial efficacy of the spray has been improved by adding aspirin ester, cinnamic acid, quinic acid, citric acid, and hydrogen peroxide into very low concentration watery solutions, mixing in $CaF_2$ oversaturated with Javel water, all finally stabilized with citric acids.

The different components act differently and the resulting spray shows excellent short time action of >log 7 and long time persistency of >log 3.

| Test Microbes | Time 1 Min [log-grade] | Time 5 Min [log-grade] |
|---|---|---|
| Staphylococcus aureus | >7.00 | >7.00 |
| Pseudomonas aeruginosa | >7.26 | >7.26 |
| Candida albicans | >4.87 | >4.87 |
| Aspergillus niger | | >4.61 |

| Component | Microbial Efficacy | Duration of Effects |
|---|---|---|
| $H_2O$ (water) | none, carrier only | |
| $CaF_2$ (calcium fluoride) | bactericide, virucide, fungicide | medium to extreme long |
| Cinnamic acid | bactericide, virucide, fungicide | short to long |
| Aspirin ester | bactericide, virucide, fungicide | short to long |
| Quinic acid | bactericide, virucide, fungicide | short to medium |
| NaOCl (Javel water) | bactericide, virucide, fungicide | short to medium |
| $H_2O_2$ (hydrogen peroxide) | bactericide, virucide, fungicide | short |
| Citric acid | bactericide, virucide, fungicide | short to medium | short = within 60 sec up to max 5 min
medium = over 5 min up to 1 hour
long = over 1 hour up to 4 hours
extreme long = over 4 hours Toxicology Data Acute Toxicology of Active Components:

| Component | mg/l | In Application [mg/3 ml] | LD 50 Oral on Rats [mg/kg] |
|---|---|---|---|
| $CaF_2$ (calcium fluoride) | 50 | 0.15 | 4500 |
| Cinnamic acid | 500 | 1.5 | 2500 |
| Aspirin ester | 2500 | 7.5 | 200 |
| Quinic acid | 1000 | 3.0 | >8000 |
| NaOCl (Javel water) | 750 | 2.25 | 2000 |
| $H_2O_2$ (hydrogen peroxide) | 12000 | 36 | 2000 |
| Citric acid | 4000 | 12.6 | 3000 |

Permitted toxicity levels for all agents are far above actual application. The product will never have toxic effects in humans, even not in repeated use.
On the skin: NO irritation
Allergization: NO allergizations reported.

| Natural Origins of Active Agents for Disinfection and Medical Cosmetics | |
|---|---|
| Agent | Origins |
| Calcium fluoride | from the mountains: as mineral fluorspar |
| Cinnamic acid | from plants: barks, flowers, tanning agents cinnamon, aniseed, chamomile |
| Aspirin ester | from plants: barks, tanning agents willow tree, bamboo, ribwort |
| Quinic acid | from plants: barks, flowers, tanning agents cinchona bark, stinging nettles cranberry, blueberry, generally from the fruits of a lot of shrubs |
| Citric acid | from plants: pins of most pinewoods citrus, berries, fruits, mushrooms |
| Alginate | from the sea: brown alga crust |
| Sea salt | from the sea: e.g. from the Dead Sea |

EXAMPLE 2

Formulation for $CaF_2$-Based Wound Gel (1000 g)

| Alginate | 23 g | 2.3% | skin/tissue cure |
|---|---|---|---|
| Salicylic acid ester | 6 g | 0.6% | fungicide |
| Ethanol | 20 g | 2.0% | log 6, fast acting |
| $CaF_2$ | 5 g | 0.5% | log 3, persistent |
| CaSO4 | 3 g | 0.3% | skin/tissue cure |
| Pure water | 944 g | 99.4% | |

EXAMPLE 3

Formulation for CaF$_2$-Based Hair Gel (1000 g)

| | | | |
|---|---|---|---|
| Alginate | 17 g | 1.7% | skin/tissue cure |
| Salicylic acid ester | 6 g | 0.6% | fungicide |
| Isopropyl alcohol | 13 g | 1.3% | log 6, fast acting |
| CaF$_2$ | 5 g | 0.5% | log 3, persistent |
| CaSO$_4$ | 2 g | 0.2% | skin/tissue cure |
| Pure water | 957 g | 95.7% | |

EXAMPLE 4

Formulation for CaF$_2$-Based Medical Hand Disinfection Spray (1000 g)

| | | | |
|---|---|---|---|
| Alginate | 3 g | 0.3% | skin/tissue cure |
| Salicylic acid ester | 6 g | 0.6% | fungicide |
| Ethanol (pharma grade) | 100 g | 10.0% | log 6, fast acting |
| Javel water | 8 g | 0.8% | log 6, fast acting |
| CaF$_2$ | 3 g | 0.3% | log 3, persistent |
| CaSO$_4$ | 1 g | 0.1% | skin/tissue cure |
| Pure water | 879 g | 87.9% | |

The persistent antiseptics of the present invention may be used in a variety of forms. For example, the compounds may be added to paint, varnish, plaster, or gypsum to produce structural surfaces having antiseptic and/or fungicidal properties. They may be produced in conventional gel or cream form providing their antiseptic infection-preventing properties in a manner for easy application to the skin. They may be added to common alginate containing components like calcium alginate to produce medical healing and curing creams for open skin wounds or dry skin. They may be added to aqueous gels to produce hair care compounds which act as protection against dryness, rough surface, and microbes. They may be mixed with water and a small percentage of alcohol for use in an automatic dispenser or nebulizer. They may be mixed with latex solutions for use in outdoor applications such as spraying fruit trees against blight. They may be mixed with drinking water for provision to animals which are otherwise easily infested by microbes, such as European honeybees. They may be applied to rubber and polymer as a filler or sealing agent for use in such products as handgrips and handlebars, elevator handrails, and the like, thereby providing persistent protection against bacterial proliferation.

Having thus described our invention, we claim:

1. A composition for spraying human skin to provide persistent antimicrobial activity, consisting of water, calcium fluoride, sodium hypochlorite, and an antimicrobial substance chosen from the group consisting of aspirin ester, cinnamic acid, quinic acid, citric acid, and hydrogen peroxide.

2. A composition for spraying human skin to provide persistent antimicrobial activity, consisting of water calcium fluoride and an antimicrobial substance chosen from the group consisting of aspirin ester, cinnamic acid, quinic acid, citric acid, and hydrogen peroxide.

3. The method of treating human and animal skin to provide persistent antimicrobial activity, comprising:
spraying the skin with a solution consisting of water calcium fluoride and an antiseptic.

4. The method of claim 3 wherein the antiseptic comprises sodium hypochlorite.

5. The method of claim 3 wherein the antiseptic comprises ethanol.

6. The method of claim 3 wherein the calcium fluoride comprises fluorspar having a fineness of less than about 5 microns.

7. The method of claim 3 wherein the antiseptic comprises an antimicrobial substance chosen from at least one of the group consisting of aspirin ester, cinnamic acid, quinic acid, citric acid, and hydrogen peroxide.

8. The method of claim 3 wherein the water in the aqueous solution exceeds 95%.

9. The method of treating human and animal skin to provide persistent antimicrobial activity, comprising:
spraying the skin with an aqueous solution of calcium fluoride comprising fluorspar having a fineness of less than about 5 microns, sodium hypochlorite, and an antimicrobial substance chosen from at least one of the group consisting of aspirin ester, cinnamic acid, quinic acid, citric acid, and hydrogen peroxide.

* * * * *

UNITED STATES PATENT AND TRADEMARK OFFICE
CERTIFICATE OF CORRECTION

PATENT NO.           : 8,445,030 B2
APPLICATION NO.      : 12/882296
DATED                : May 21, 2013
INVENTOR(S)          : Fridolin Voegeli et al.

It is certified that error appears in the above-identified patent and that said Letters Patent is hereby corrected as shown below:

In the Specifications:
At column 1, line number 24, insert --that-- after the word disinfectants.
At column 2, line number 32, replace "microorganism" with --microorganisms--.
At column 3, line number 17, replace "$CaF_2+$" with --$CaF_2$--.

In the Claims:
At column 6, claim number 3, line number 23, insert a --,-- after the word water.

Signed and Sealed this
Twentieth Day of August, 2013

Teresa Stanek Rea
*Acting Director of the United States Patent and Trademark Office*